United States Patent
Toriyabe et al.

(10) Patent No.: US 9,687,421 B2
(45) Date of Patent: Jun. 27, 2017

(54) DENTAL FILING AND RESTORATIVE MATERIAL KIT

(71) Applicants: Chika Toriyabe, Tokyo (JP); Hironobu Akizumi, Tokyo (JP)

(72) Inventors: Chika Toriyabe, Tokyo (JP); Hironobu Akizumi, Tokyo (JP)

(73) Assignee: TOKUYAMA DENTAL CORPORATION, Tokyo (JP)

( * ) Notice: Subject to any disclaimer, the term of this patent is extended or adjusted under 35 U.S.C. 154(b) by 0 days.

(21) Appl. No.: 14/772,604

(22) PCT Filed: Mar. 10, 2014

(86) PCT No.: PCT/JP2014/056164
§ 371 (c)(1),
(2) Date: Sep. 3, 2015

(87) PCT Pub. No.: WO2014/148293
PCT Pub. Date: Sep. 25, 2014

(65) Prior Publication Data
US 2016/0008232 A1    Jan. 14, 2016

(30) Foreign Application Priority Data

Mar. 19, 2013  (JP) ................................. 2013-056245

(51) Int. Cl.
*A61K 6/00*  (2006.01)
*A61K 6/083*  (2006.01)
*C08L 33/10*  (2006.01)

(52) U.S. Cl.
CPC ............ *A61K 6/0005* (2013.01); *A61K 6/083* (2013.01)

(58) Field of Classification Search
None
See application file for complete search history.

(56) References Cited

U.S. PATENT DOCUMENTS

| | | | | |
|---|---|---|---|---|
| 2,326,736 A * | 8/1943 | Adelson | ..................... | C08F 2/46 522/178 |
| 6,174,935 B1 * | 1/2001 | Matsunae | ............ | A61K 6/0029 206/63.5 |
| 7,452,487 B2 * | 11/2008 | Kanzaki | ................. | B01D 71/40 205/637 |
| 7,614,879 B2 * | 11/2009 | Nemoto | ............... | A61K 6/0029 106/35 |
| 8,946,318 B2 * | 2/2015 | Akizumi | ................ | C08L 33/10 433/228.1 |
| 2007/0066748 A1 * | 3/2007 | Lewandowski | ...... | A61K 6/0017 524/556 |
| 2009/0298966 A1 * | 12/2009 | Vanini | .................. | A61K 6/0276 523/116 |
| 2014/0017638 A1 * | 1/2014 | Akizumi | ................ | C08L 33/10 433/228.1 |
| 2016/0008232 A1 * | 1/2016 | Toriyabe | ................ | A61K 6/083 523/115 |

FOREIGN PATENT DOCUMENTS

| | | |
|---|---|---|
| JP | 09169613 A | 6/1997 |
| JP | 11100305 A | 4/1999 |
| JP | 2007082679 A | 4/2007 |
| JP | 2008508930 A | 3/2008 |
| WO | 2012128167 A1 | 9/2012 |

OTHER PUBLICATIONS

Bis(2-methacryloxyethyl) phosphate, Chemical Book, Jan. 27, 2016.*
Refractive Index of Methacrylate Monomers and Polymers, Esstech Inc. Mar. 12, 2010.*
H. Matsumura et al.,"Adhesion Yearbook 2006", first edition, Quintessence Publishing Co., Ltd., Aug. 2006, p. 129-137.
International Search Report corresponding to Application No. PCT/JP2014/056164; Date of Mailing: Jun. 3, 2014, with English translation.
M. Miyazaki et al., "Science & Technique of Composite Resin Restoration", first edition, Quintessence Publishing Co., Ltd., Jan. 2010, p. 48-49.

* cited by examiner

Primary Examiner — Peter A Salamon
(74) Attorney, Agent, or Firm — Cantor Colburn LLP

(57) ABSTRACT

Provided is a dental filling and restorative material kit, including: a polymerizable composition (A) for a dentin restorative material for restoring a dentin portion; and a polymerizable composition (B) for an enamel restorative material to be layered on the dentin restorative material, in which the polymerizable composition (A) for a dentin restorative material and the polymerizable composition (B) for an enamel restorative material have different color tones, and in which a difference ($n_D^a - n_D^b$) between a refractive index $n_D^a$ of a polymer of a polymerizable monomer (a) in the polymerizable composition (A) for a dentin restorative material and a refractive index $n_D^b$ of a polymer of a polymerizable monomer (b) in the polymerizable composition (B) for an enamel restorative material is 0.005 or more.

9 Claims, No Drawings

DENTAL FILING AND RESTORATIVE MATERIAL KIT

CROSS REFERENCE TO RELATED APPLICATIONS

This is the U.S. national stage of application No. PCT/JP2014/056164, filed on Mar. 10, 2014. Priority under 35 U.S.C. §119 (a) and 35 U.S.C. §365(b) is claimed from Japanese Application No. 2013-056245, filed Mar. 19, 2013, the disclosure of which is also incorporated herein by reference.

TECHNICAL FIELD

The present invention relates a dental filling and restorative material kit.

BACKGROUND ART

In restoration of a tooth damaged by caries, fracture, or the like, a restorative material called a composite resin, which is formed of a polymerizable composition (which is generally photocurable) in a paste form, is widely used because the restorative material allows a simple operation. In recent years, the polymerizable composition has been improved in mechanical strength and also in adhesive force for a tooth, and hence has been used for not only restoration of an anterior tooth portion, but also a posterior tooth portion, to which a high occlusal pressure is applied. The restoration of a tooth using the dental restorative material is generally performed by a method involving:
1) forming a cavity in a tooth damaged by caries or the like (hereinafter sometimes referred to as "tooth to be restored") by cutting;
2) building up the polymerizable composition in the cavity through intermediation of an adhesive (in general, an adhesive called a bonding material is applied to the cavity, and as necessary, an air blow is performed, followed by photoirradiation to cover the cavity with the adhesive), followed by photocuring to seal the cavity; and
3) finally subjecting the cured body of the composite filling and restorative material with which the cavity is filled to shape modification and polishing.

The restoration of a tooth requires satisfactory aesthetics in addition to operability, mechanical strength, and the like. A natural tooth is formed of dentin and enamel, and its color tone is almost entirely derived from the dentin, which is observed through the transparent enamel. It should be noted that the enamel increases from a tooth cervical portion toward an incisal portion, and the color tone (at least one kind of element selected from a hue, a chroma, and a lightness) differs from site to site. For example, the tooth cervical portion has a thick dentin layer, and hence is opaque and has high values for the lightness (light and shade of color) and the chroma (intensity of color) as compared to the incisal portion. In contrast, the incisal portion has a thin dentin layer and is almost entirely formed of the enamel, and hence has high transparency. As described above, the color tone of a tooth differs from site to site. Accordingly, in order to obtain high aesthetics in the restoration of a tooth, it is important to prepare a plurality of kinds of polymerizable compositions having different color tones, and to use one selected therefrom and having a color tone that best conforms to those of an actual tooth to be restored and teeth adjacent thereto (hereinafter sometimes referred to as "surroundings of the tooth to be restored") (Non Patent Literature 1).

A dentist performs such color tone selection with a shade guide (color sample), which is a collection of respective cured body samples of prepared polymerizable compositions, by comparing the color tone of each of the samples to the color tone of the surroundings of the tooth to be restored, which is checked by looking into the mouth, and selecting the one considered to have the color tone closest to that of the surroundings of the tooth to be restored.

In addition, unless the damage of the tooth to be restored is light and the cavity is shallow, the conformation of the color tone is difficult to achieve by filling with a single kind of polymerizable composition. That is, when the cavity is deep (e.g., a class IV cavity), the color tone of the tooth is observed not merely as the color tone of a tooth surface portion (enamel portion) but in a gradation-rich state in which color tones, even including that of a deep portion (dentin portion) that can be seen through, are blended. Accordingly, such subtle color tone is reproduced by layered filling, which involves changing the color tone of the polymerizable composition to be filled at certain depth intervals. In general, a plurality of kinds of polymerizable compositions for a dentin portion restorative material, which reproduce the color tone of the dentin portion, are layered from the deepest portion (each layer is generally cured before further layering), and finally, a polymerizable composition for an enamel portion restorative material is layered as a surface layer portion (see, for example, Non Patent Literature 1 and Non Patent Literature 2).

Further, there is also a proposal of a material that is conformed to a natural tooth in terms of optical characteristics as well as color tone ((Patent Literature 1). With a focus on a light-diffusing property, it is reported that restoration with good aesthetics can be performed by using a material having a high light-diffusing property for a portion including a large amount of dentin and using a material having a low light-diffusing property and a high transmissivity for a portion including a large amount of enamel.

In addition, there is also a report of a dental restorative material having its refractive index adjusted. In Patent Literature 2, refractive indices of a dentin restorative material and an enamel restorative material are adjusted to be similar to each other. In Patent Literature 3, an enamel restorative material is adjusted to have a high refractive index in order to reproduce optical characteristics of a natural tooth.

CITATION LIST

Patent Literature

[PTL 1] JP 9-169613 A
[PTL 2] JP 2007-082679 A
[PTL 3] JP 2009-508930 A

Non Patent Literature

[NPL 1] "Adhesion YEARBOOK 2006", edited by Hideo Matsumura and Junji Tagami, first edition, Quintessence Publishing Co., Ltd., August, 2006, p. 129-137
[NPL 2] "Science & Technique of Composite Resin Restoration", written by Masashi Miyazaki, first edition, Quintessence Publishing Co., Ltd., January, 2010, p. 48-49

SUMMARY OF INVENTION

Technical Problem

However, in general, in order to achieve higher aesthetics, it is necessary to provide satisfactory color tone conformability to a natural tooth, and also to prevent, when layering an enamel restorative material on a dentin restorative material, the enamel restorative material from being darkened owing to the influence of a background color in the mouth. When the enamel restorative material looks darkened owing to the influence of the background color, there arises a problem of a reduction in aesthetics, or a problem of difficulty in seeing a structure unique to dentin due to the darkening, which causes a reduction in aesthetics.

Particularly in such a large cavity as to penetrate through from a labial side to a lingual side like a class IV cavity in an anterior tooth, it is extremely important from the viewpoint of aesthetic restoration to reproduce optical characteristics called a mamelon found in an incisal portion. In such cavity, restoration with satisfactory aesthetics is difficult even with a material having its light-diffusing property controlled, and it has been necessary to perform a complicated working process such as layering a plurality of kinds of polymerizable compositions having different color tones for each of a dentin portion restorative material and an enamel portion restorative material. It should be noted that the mamelon is an internal structure found in the incisal portion and formed of dentin, and is found as a finger-like structure. A jagged shape on the incisal side of a dentin layer is recognized through the enamel as a surface layer.

That is, in order to perform restoration with high aesthetics in the incisal portion, filling with a plurality of kinds of polymerizable compositions having different color tones (for example, a total of four kinds of polymerizable compositions including two kinds of polymerizable compositions for a dentin restorative material and two kinds of polymerizable compositions for an enamel restorative material) needs to be performed within a limited thickness of 2 mm or less, and hence an operator is required to be highly skilled in filling.

Meanwhile, in order to provide satisfactory color tone conformability between a tooth to be restored and the restorative materials, the dentin restorative material and the enamel restorative material each need to have a color tone within a certain range. Particularly when a contrast ratio, which is one element of the color tone, is adjusted to be high in the dentin restorative material (opaque) and low in the enamel restorative material (transparent) so as to conform to the color tone of a natural tooth, a lifelike restoration having high color tone conformability to the tooth to be restored and being transparent can be obtained. However, particularly in the incisal portion, an enamel restorative material increased in transparency is liable to be darkened (be reduced in lightness) owing to, for example, the influence of the background color in the mouth, and consequently, the color tone of the underlying dentin restorative material is shielded, which makes it difficult to reproduce the characteristic structure of the dentin, resulting in poor aesthetics. That is, it has been desired to develop a restorative material that has satisfactory color tone conformability to a natural tooth despite a small number of kinds of polymerizable compositions for filling and in which a reduction in lightness is suppressed.

The present invention has been made in view of the above-mentioned circumstances, and an object of the present invention is to provide a dental filling and restorative material kit that allows the restoration of a tooth to be performed with satisfactory color tone conformability and little reduction in lightness, thus enabling restoration with high aesthetics, and more particularly, to provide a dental filling and restorative material kit that allows even the characteristic structure of dentin to be reproduced even in a cavity in which a background color tone can be seen through.

Solution to Problem

The inventors of the present invention have continuously conducted extensive investigations in order to achieve the above-mentioned technical object.

As a result, the inventors have found that the above-mentioned object can be achieved by causing the refractive indices of polymers of polymerizable monomers contained in a polymerizable composition for a dentin restorative material and a polymerizable composition for an enamel restorative material, respectively, to have a specific relationship. Thus, the inventors have completed the present invention.

That is, a dental filling and restorative material kit of the present invention includes: a polymerizable composition (A) for a dentin restorative material for restoring a dentin portion; and a polymerizable composition (B) for an enamel restorative material to be layered on the dentin restorative material, in which the polymerizable composition (A) for a dentin restorative material and the polymerizable composition (B) for an enamel restorative material have different color tones, and in which a difference $(n_D^a - n_D^b)$ between a refractive index $n_D^a$ of a polymer of a polymerizable monomer (a) in the polymerizable composition (A) for a dentin restorative material and a refractive index $n_D^b$ of a polymer of a polymerizable monomer (b) in the polymerizable composition (B) for an enamel restorative material is 0.005 or more.

In a dental filling and restorative material kit according to one embodiment of the present invention, it is preferred that the dental filling and restorative material kit consist of the polymerizable composition (A) for a dentin restorative material and the polymerizable composition (B) for an enamel restorative material.

In a dental filling and restorative material kit according to another embodiment of the present invention, it is preferred that a 1-mm cured body of the polymerizable composition (A) for a dentin restorative material have a contrast ratio of from 0.55 to 0.75, and a 1-mm cured body of the polymerizable composition (B) for an enamel restorative material have a contrast ratio of from 0.30 to 0.54.

Advantageous Effects of Invention

The use of the dental filling and restorative material kit of the present invention allows the restoration of a tooth to be performed with satisfactory color tone conformability and little reduction in lightness, thus enabling restoration with high aesthetics. In particular, even the characteristic structure of dentin can be reproduced even in a cavity in which a background color tone can be seen through.

DESCRIPTION OF EMBODIMENTS

A dental filling and restorative material kit according to one embodiment of the present invention includes: a polymerizable composition (A) for a dentin restorative material for restoring a dentin portion; and a polymerizable composition (B) for an enamel restorative material to be layered on the dentin restorative material. In addition to, the dental filling and restorative material kit according to this embodiment has a feature in that the polymerizable composition (A) for a dentin restorative material and the polymerizable composition (B) for an enamel restorative material have different color tones, and a difference ($n_D^a - n_D^b$) between a refractive index $n_D^a$ of a polymer of a polymerizable monomer (a) in the polymerizable composition (A) for a dentin restorative material and a refractive index $n_D^b$ of a polymer of a polymerizable monomer (b) in the polymerizable composition (B) for an enamel restorative material is 0.005 or more. It should be noted that the dental filling and restorative material kit according to this embodiment uses the polymerizable composition (A) for a dentin restorative material that contains the polymerizable monomer (a), and the polymerizable composition (B) for an enamel restorative material that contains the polymerizable monomer (b), and the refractive indices are specified as the refractive indices $n_D^a$ and $n_D^b$ of polymers after the polymerization of the respective polymerizable monomers.

That is, as described above, the dental filling and restorative material kit according to this embodiment has a feature in that the refractive index of the polymer forming the dentin restorative material is set higher than the refractive index of the polymer forming the enamel restorative material by 0.005 or more. On the other hand, in the case of a natural tooth, the refractive index of enamel (about 1.63) is higher than the refractive index of dentin (about 1.55). This relationship is completely opposite to that in the dental filling and restorative material kit according to this embodiment. The dentin and enamel of the natural tooth are not distinctly separated, and a transitional boundary layer is formed between the dentin and the enamel. The boundary layer is considered to play an important role in aesthetics. Therefore, in order to completely imitate the natural tooth, the boundary layer also needs to be imitated inclusively. However, such system is complicated, and even the boundary layer itself is difficult to imitate. In addition, it has been difficult to obtain natural tooth-like aesthetics by merely making the refractive indices of the dentin restorative material and the enamel restorative material, excluding the boundary layer, closer to those of the natural tooth. Against such background, it has been found that a restoration with good aesthetics is obtained on the basis of the concept of setting the refractive index of the dentin restorative material higher than the refractive index of the enamel restorative material, which is completely opposite to the viewpoint of natural tooth imitation.

A description is given below of a possible mechanism of the expression of such an effect that a restoration with good aesthetics is obtained when the dental filling and restorative material kit according to this embodiment is used.

First, the refractive indices of the polymers of the respective polymerizable monomers included in the dental filling and restorative material kit according to this embodiment have the specific relationship described above. Accordingly, light transmitted from the surface of the enamel restorative material is reflected at an interface between both the materials, i.e., the enamel restorative material and the dentin restorative material, and the reflected light is transmitted through the enamel restorative material again to be visually observed. As a result, a reduction in lightness due to the enamel restorative material is suppressed, and besides, the characteristic structure of the dentin can be visually recognized. Presumably as a result of the foregoing, restoration with satisfactory aesthetics can be performed.

In addition, in the dental filling and restorative material kit according to this embodiment, the refractive index of the enamel restorative material is set relatively low, and the refractive index of the dentin restorative material is set relatively high. Meanwhile, in general, a light reflectance increases as the refractive index of an object becomes higher. Accordingly, when the refractive index of the enamel restorative material is set lower, the reflection of light by the surface of the enamel restorative material is reduced, and consequently, the amount of light transmitted to the inside of the enamel restorative material is increased. Therefore, the amount of light reflected at the interface between both the materials, i.e., the enamel restorative material and the dentin restorative material is increased as a result, which is considered to result in satisfactory aesthetics.

Next, various physical property values related to a color tone, which are used in the dental filling and restorative material kit according to this embodiment, are described.

<Lightness (L*)>

A lightness (L*) is an indicator of brightness and is measured as specified in JIS Z8729. Specifically, a sample plate having a thickness of 1.0 mm is brought into contact with a black background and irradiated with standard light C. An L* value expressed in the CIELab color system in reflected light in this case is read. An L* value closer to 100 indicates a brighter material, and an L* value closer to 0 indicates a darker material.

<Chromaticity (a*) (b*)>

Chromaticity is an indicator of a hue and a chroma and is measured as specified in JIS Z8729. Specifically, a sample plate having a thickness of 1.0 mm is brought into contact with a black background and irradiated with standard light C. An a* value and b* value expressed in the CIELab color system in reflected light in this case are read. a* and b* represent directions of color, a* represents a red direction, –a* represents a green direction, b* represents a yellow direction, and –b* represents a blue direction. A larger value in each direction indicates a more intense color, and a smaller value in each direction indicates a duller color.

<Contrast Ratio>

A contrast ratio is an indicator of transparency and is calculated using a Y value, which is related to brightness, of the tristimulus values of the XYZ color system specified in JIS 28701. Specifically, a sample plate having a thickness of 1.0 mm is brought into contact with each of a black background and a white background, and irradiated with standard light C. A Y value in reflected light in this case is read. When Y in the case of the black background and Y in the case of the white background are represented by Yb and Yw, respectively, the contrast ratio (C) is determined by Yb/Yw. AC value closer to 1 indicates a more opaque material, and a C value closer to 0 indicates a more transparent material.

The dental filling and restorative material kit according to this embodiment only needs to include: the polymerizable composition (A) for a dentin restorative material for restoring a dentin portion (hereinafter sometimes referred to simply as "polymerizable composition for a dentin restorative material"); and the polymerizable composition (B) for an enamel restorative material to be layered on the dentin restorative material (hereinafter sometimes referred to simply as "polymerizable composition for an enamel restorative material"). For example, the dental filling and restorative material kit according to this embodiment may further include any other composition than the polymerizable composition for a dentin restorative material and the polymerizable composition for an enamel restorative material. However, the dental filling and restorative material kit according to this embodiment may consist only of the polymerizable composition for a dentin restorative material and the polymerizable composition for an enamel restorative material.

In addition, the dental filling and restorative material kit according to this embodiment may be a kit including one kind of polymerizable composition for a dentin restorative material, and one kind of polymerizable composition for an enamel restorative material. However, the dental filling and restorative material kit according to this embodiment is preferably a kit including one or more kinds of polymerizable compositions for a dentin restorative material, and one or more kinds of polymerizable compositions for an enamel restorative material. In this case, at least one kind of polymerizable composition P for a dentin restorative material selected from m kinds of polymerizable compositions for a dentin restorative material, and at least one kind of polymerizable composition Q for an enamel restorative material selected from n kinds of polymerizable compositions for an enamel restorative material only need to satisfy the following conditions <I> and <II>. In this case, m and n each represent an integer of 1 or more. When m represents 2 or more, the m kinds of polymerizable compositions for a dentin restorative material differ from each other in color tone, and when n represents 2 or more, the n kinds of polymerizable compositions for an enamel restorative material differ from each other in chromaticity.

<I> The polymerizable composition P for a dentin restorative material and the polymerizable composition Q for an enamel restorative material have different color tones.

<II> A difference $(n_D^a - n_D^b)$ between a refractive index $n_D^a$ of a polymer of a polymerizable monomer (a) in the polymerizable composition P for a dentin restorative material and a refractive index $n_D^b$ of a polymer of a polymerizable monomer (b) in the polymerizable composition Q for an enamel restorative material is 0.005 or more.

It should be noted that m preferably represents an integer selected from the range of from 1 to 20, and in practical use, more preferably represents an integer selected from the range of from 2 to 20, and n also preferably represents an integer selected from the range of from 1 to 20, and in practical use, more preferably represents an integer selected from the range of from 2 to 20. In addition, in the combinations of the m kinds of polymerizable compositions for a dentin restorative material and the n kinds of polymerizable compositions for an enamel restorative material, at least one combination that satisfies the conditions <I> and <II> only needs to exist as described above. However, when m+n is 3 or more, it is preferred that two or more combinations that satisfy the conditions <I> and <II> exist, and it is particularly preferred that all combinations (m×n combinations) satisfy the conditions <I> and <II>. In addition, as the numbers m and n, and the number of combinations that satisfy the conditions <I> and <II> increase as just described, it becomes easier to perform restoration with high aesthetics conformed to the teeth of a patient.

In addition, in the dental filling and restorative material kit according to this embodiment, the dentin restorative material refers to a cured body of the polymerizable composition for dentin restoration material, and the enamel restorative material refers to a cured body of the polymerizable composition for an enamel restorative material. In the dental filling and restorative material kit according to this embodiment, a mode of layering is not particularly limited, and it is meant that the enamel restorative material only needs to be arranged on the dentin restorative material as a result. That is, the polymerizable composition for a dentin restorative material may be cured to form the dentin restorative material before the polymerizable composition for an enamel restorative material is filled and cured on the dentin restorative material, or the polymerizable composition for an enamel restorative material may be filled on the polymerizable composition for a dentin restorative material before both the polymerizable compositions are cured. It should be noted that those two kinds of polymerizable compositions may each adopt any form such as a paste form, a liquid form, a powder form, or a jelly form, but a paste form is particularly preferred.

In addition, the polymerizable composition for a dentin restorative material and polymerizable composition for an enamel restorative material included in the dental filling and restorative material kit according to this embodiment have different color tones. It is intended that their color tones are conformed to those of the enamel and dentin of a human tooth to be restored. Herein, having different color tones means having a difference in any one index out of a*, b*, and L* in the CIELab color system and the contrast ratio. For example, when the color tone of the polymerizable composition for a dentin restorative material has an a* of −2, a b* of 12, and an L* of 60, whereas the color tone of the polymerizable composition for an enamel restorative material has an a* of −2, a b* of 12, and an L* of 48, their relationship has no difference in a* or b*, and has a difference only in L*, but their color tones are recognized as different.

In consideration of color tone conformability, when the polymerizable composition for a dentin restorative material and polymerizable composition for an enamel restorative material included in the dental filling and restorative material kit according to this embodiment are each subjected to color measurement in the CIELab color system, a* is set within the range of from −5.0 to 3.0, more suitably within the range of from −4.0 to 2.0. On the other hand, b* is set within the range of from −10 to 20, more suitably within the range of from −9 to 19. In addition, when there is a difference in a* or b* between both the polymerizable compositions, the absolute value of the difference in a* falls within the range of from 0.1 to 4, preferably from 0.3 to 2, and the absolute value of the difference in b* falls within the range of from 0.1 to 30, preferably from 0.3 to 15.

The lightness L* of the polymerizable composition for a dentin restorative material included in the dental filling and restorative material kit according to this embodiment is selected from the range of from 50 to 75, more suitably from 51 to 74. On the other hand, the L* of the polymerizable composition for an enamel restorative material is selected from the range of from 40 to 55, more suitably from 41 to 54. When both the polymerizable compositions have different L* values, the difference in L* between both the polymerizable compositions (lightness L* of polymerizable composition for a dentin restorative material-lightness L* of polymerizable composition for an enamel restorative material) falls within the range of from 1 to 30, preferably the range of from 3 to 20.

In addition, the color tone of a 1-mm cured body of the polymerizable composition for a dentin restorative material (the 1-mm cured body means a cured body having a thickness of 1 mm obtained by curing a polymerizable composition) under a black background condition in color measurement in the CIELab color system has a contrast ratio selected from the range of preferably from 0.55 to 0.75, more preferably from 0.57 to 0.70. Further, in the polymerizable composition for an enamel restorative material, the contrast ratio is preferably selected from the range of from 0.30 to 0.54, more suitably from the range of preferably from 0.35 to 0.52. The polymerizable composition for a dentin restorative material and the polymerizable composition for an enamel restorative material preferably differ in transparency. Specifically, a difference in contrast ratio between both the polymerizable compositions (contrast ratio of polymerizable composition for a dentin restorative material-contrast ratio of polymerizable composition for an enamel restorative material) falls within preferably the range of from 0.05 to 0.40, more preferably the range of from 0.10 to 0.30. When the contrast ratios fall within this range, the transparency of each of the polymerizable compositions well conforms to the transparency of each of the enamel and dentin of a natural tooth. When the contrast ratios are controlled as described above, an effect described below is remarkably exhibited. That is, in general, when the contrast ratio is controlled as described above, although color tone conformability to a natural tooth is satisfactory, aesthetics tends to be reduced owing to, for example, darkening of an enamel restoration portion or unrecognizability of the characteristic structure of dentin. However, the refractive indices of the polymers of the respective polymerizable monomers contained in the polymerizable composition for a dentin restorative material, and the polymerizable composition for an enamel restorative material are adjusted within the specific range as in the dental filling and restorative material kit according to this embodiment, the above-mentioned problem of the reduction in aesthetics is eliminated. Specifically, a dentin restorative material having a high contrast ratio has a high lightness, and hence the amount of light to be reflected at an interface between the dentin restorative material and the enamel restorative material is increased. Further, when the enamel restorative material to be layered on the dentin restorative material has a low contrast ratio, the light reflected at the interface is easily transmitted therethrough, and hence a mamelon can be expressed more effectively.

In addition to the polymerizable composition (A) for a dentin restorative material and polymerizable composition (B) for an enamel restorative material included in the dental filling and restorative material kit according to this embodiment, the dental filling and restorative material kit may include a polymerizable composition having a special color tone in order to better conform the color tones of a human tooth to be restored and the restorative material to each other. Specific examples thereof include: a polymerizable composition having a high lightness (L* of more than 75) and having a white color, which is suited to an opaque and white tooth after bleaching treatment; and a polymerizable composition having a contrast ratio of less than 0.3 and having a transparent color, which is suited to a tooth having high transparency.

In the dental filling and restorative material kit having such color tones, there are used composite resins each of which is adopted from general dental restorative materials and formed of a polymerizable monomer, a polymerization initiator, a filler, and a colorant.

The greatest feature of the dental filling and restorative material kit according to this embodiment resides in that the polymers of the respective polymerizable monomers contained in the polymerizable composition (A) for a dentin restorative material and the polymerizable composition (B) for an enamel restorative material have different refractive indices. Specifically, the greatest feature resides in that the difference ($n_D^a - n_D^b$) between the refractive index $n_D^a$ of the polymer of the polymerizable monomer (a) in the polymerizable composition (A) for a dentin restorative material and the refractive index $n_D^b$ of the polymer of the polymerizable monomer (b) in the polymerizable composition (B) for an enamel restorative material is 0.005 or more. When the refractive indices are controlled as just described, restoration with satisfactory aesthetics can be performed. In particular, even in restoration at a restoration site such as an incisal portion, where the polymerizable composition for a dentin restorative material is thinly filled and the polymerizable composition for an enamel restorative material is thickly layered as compared to the polymerizable composition for a dentin restorative material, namely, a site where the enamel restorative material is liable to be influenced by a background color in the mouth, the characteristic structure of dentin (mamelon) can be reproduced, and restoration with satisfactory aesthetics can be performed. When the refractive index difference is less than 0.005, the enamel restorative material tends to be a dark restoration, and the characteristic structure of dentin formed of the dentin restorative material is difficult to visually recognize, resulting in poor aesthetics. The refractive index difference ($n_D^a - n_D^b$) is preferably 0.007 or more, more preferably 0.009 or more. Meanwhile, polymerizable monomers to be used in dentistry are limited from the viewpoint of safety, and an upper limit for the refractive index difference that may be attained with polymerizable monomers to be generally used in dentistry is about 0.15. In addition, when the refractive index difference is excessively large, the reflection of light at the interface is also increased, and the characteristic structure of the dentin (mamelon) becomes conspicuous, with the result that harmony with the surroundings of the tooth to be restored may not be achieved. Therefore, the refractive index difference ($n_D^a - n_D^b$) is preferably 0.15 or less, more preferably 0.065 or less, still more preferably 0.05 or less, particularly preferably 0.03 or less. The refractive indices of the polymers of the polymerizable monomers suitable for the respective polymerizable compositions may be appropriately selected and used as long as the above-mentioned refractive index difference is satisfied. Specifically, the refractive index of the polymer of the polymerizable monomer to be used for the polymerizable composition for a dentin restorative material is selected from the range of preferably from 1.53 to 1.60, more suitably from 1.54 to 1.58. On the other hand, the refractive index of the polymer of the polymerizable monomer to be used for the polymerizable composition for an enamel restorative material is selected from the range of preferably from 1.45 to 1.57, more suitably from 1.50 to 1.56.

It should be noted that the refractive indices in the dental filling and restorative material kit according to this embodiment refer to values measured with an Abbe refractometer under an atmosphere at 25° C.

Herein, it is extremely important that the refractive index $n_D^a$ of polymer of the polymerizable monomer (a) in the polymerizable composition (A) for a dentin restorative material be higher than the refractive index $n_D^b$ of the polymer of the polymerizable monomer (b) in the polymerizable composition (B) for an enamel restorative material. The refractive index of the dentin of a natural tooth (about 1.55) is lower than the refractive index of the enamel of the natural tooth (about 1.63). That is, the two kinds of polymerizable compositions included in the dental filling and restorative material kit according to this embodiment have an opposite relationship in magnitude of refractive index as compared to the dentin and enamel of the natural tooth, and thus the dental filling and restorative material kit according to this embodiment does not merely imitate the characteristics of the natural tooth.

In the dental filling and restorative material kit according to this embodiment, the respective polymerizable compositions (A) and (B) are not particularly limited as long as the refractive indices of the polymers of the polymerizable monomers contained therein fall within the respective specific ranges, and ones adopted from conventional dental restorative materials may be used. As described above, composite resins each formed of a polymerizable monomer, a polymerization initiator, a filler, and a colorant are used as general dental restorative materials.

As the polymerizable monomer, one to be used as a polymerizable monomer for a composite resin in the field of dentistry may be used without any limitation. A (meth) acrylate-based polymerizable monomer is preferred, and a polyfunctional (meth)acrylate-based polymerizable monomer is more preferred from the viewpoints of, for example, a curing rate and the mechanical physical properties, water resistance, and coloring resistance of a cured body.

Examples of the polyfunctional (meth)acrylate-based polymerizable monomer that may be suitably used include ones described in the following (I) to (III).

(I) Bifunctional Polymerizable Monomer i) Aromatic Compound-Based Bifunctional Polymerizable Monomer 2,2-Bis(methacryloyloxyphenyl)propane, 2,2-bis[4-(3-methacryloyloxy)-2-hydroxypropoxyphenyl]propane (hereinafter abbreviated as bis-GMA), 2,2-bis(4-methacryloyloxyphenyl)propane, 2,2-bis(4-methacryloyloxypolyethoxyphenyl)propane (hereinafter abbreviated as D-2.6E), 2,2-bis(4-methacryloyloxydiethoxyphenyl)propane, 2,2-bis(4-methacryloyloxytetraethoxyphenyl)propane, 2,2-bis(4-methacryloyloxypentaethoxyphenyl)propane, 2,2-bis(4-methacryloyloxydipropoxyphenyl)propane, 2-(4-methacryloyloxydiethoxyphenyl)-2-(4-methacryloyloxytriethoxyphenyl)propane, 2-(4-methacryloyloxydipropoxyphenyl)-2-(4-methacryloyloxytriethoxyphenyl)propane, 2,2-bis(4-methacryloyloxypropoxyphenyl)propane, and 2,2-bis(4-methacryloyloxyisopropoxyphenyl)propane, and acrylates corresponding to these methacrylates; diadducts each obtained by addition of a vinyl monomer having an —OH group, like a methacrylate such as 2-hydroxyethyl methacrylate, or 2-hydroxypropyl methacrylate, 3-chloro-2-hydroxypropyl methacrylate, or an acrylate corresponding to each of these methacrylates and a diisocyanate compound having an aromatic group, such as diisocyanatomethylbenzene or 4,4'-diphenylmethane diisocyanate; and the like.

ii) Aliphatic Compound-Based Bifunctional Polymerizable Monomer

Ethylene glycol dimethacrylate, diethylene glycol dimethacrylate, triethylene glycol dimethacrylate (hereinafter abbreviated as 3G), tetraethylene glycol dimethacrylate, neopentyl glycol dimethacrylate, 1,3-butanediol dimethacrylate, 1,4-butanediol dimethacrylate, 1,6-hexanediol dimethacrylate, and acrylates corresponding to these methacrylates; diadducts each obtained from an adduct of a vinyl monomer having an —OH group, like a methacrylate such as 2-hydroxyethyl methacrylate, 2-hydroxypropyl methacrylate, or 3-chloro-2-hydroxypropyl methacrylate, or an acrylate corresponding to each of these methacrylates and a diisocyanate compound, such as hexamethylene diisocyanate, trimethylhexamethylene diisocyanate, diisocyanatomethylcyclohexane, isophorone diisocyanate, or methylenebis(4-cyclohexyl isocyanate), for example, 1,6-bis(methacrylethyloxycarbonylamino)trimethylhexane (hereinafter abbreviated as "UDMA"); acrylic anhydride; methacrylic anhydride; 1,2-bis(3-methacryloyloxy-2-hydroxypropoxy)ethyl; di(2-methacryloyloxypropyl)phosphate; and the like.

(II) Trifunctional Polymerizable Monomer

Methacrylates, acrylates corresponding to the methacrylates, and the like, the methacrylates including trimethylolpropane trimethacrylate, trimethylolethane trimethacrylate, pentaerythritol trimethacrylate, and trimethylolmethane trimethacrylate.

(III) Tetrafunctional Polymerizable Monomer

Pentaerythritol tetramethacrylate, pentaerythritol tetraacrylate, diadducts each obtained from an adduct of a diisocyanate compound and glycidol dimethacrylate, and the like, the diisocyanate compound being, for example, diisocyanatomethylbenzene, diisocyanatomethylcyclohexane, isophorone diisocyanate, hexamethylene diisocyanate, trimethylhexamethylene diisocyanate, methylenebis(4-cyclohexyl isocyanate), 4,4-diphenylmethane diisocyanate, or tolylene-2,4-diisocyanate.

Cured bodies of those polyfunctional (meth)acrylate-based polymerizable monomers generally have refractive indices (25° C.) within the range of from 1.45 to 1.60. The polymerizable monomers to be used respectively for the two kinds of polymerizable compositions included in the dental filling and restorative material kit according to this embodiment are not limited to (meth)acrylate-based ones, but it suffices to appropriately select from, for example, the above-mentioned polymerizable monomers in consideration of the refractive index. In general, a polymer of an aromatic polymerizable monomer (such as D2.6E or bisGMA) tends to show a high refractive index, and a polymer of an aliphatic polymerizable monomer (such as 3G or UDMA) tends to show a low refractive index. The refractive index may be appropriately adjusted by using one kind of those polymerizable monomers alone, or using two or more kinds thereof in combination.

Further, as required, there may be used monofunctional (meth)acrylate-based monomers including methacrylates such as methyl methacrylate, ethyl methacrylate, isopropyl methacrylate, hydroxyethyl methacrylate, tetrahydrofurfuryl methacrylate, and glycidyl methacrylate, and acrylates corresponding to these methacrylates, and polymerizable monomers other than the (meth)acrylate-based monomers.

As the polymerization initiator, a known one may be used without any limitation as long as the polymerization initiator can polymerize and cure the polymerizable monomer. In general, a photopolymerization initiator is often used, but a chemical polymerization initiator (normal temperature redox initiator), a thermal polymerization initiator, or the like may also be used. One kind of the polymerization initiators may be used alone, or two or more kinds thereof may be used in combination.

As the photopolymerization initiator, for example, there may be used: benzoin alkyl ethers such as benzoin methyl ether, benzoin ethyl ether, and benzoin isopropyl ether; benzyl ketals such as benzyl dimethyl ketal and benzyl diethyl ketal; diaryl ketones such as benzophenone, anthraquinone, and thioxanthone; α-diketones such as diacetyl, benzil, camphorquinone, and 9,10-phenanthraquinone; and bisacylphosphine oxides such as bis-(2,6-dichlorobenzoyl) phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, and bis(2,4,6-trimethylbenzoyl)-phenylphosphine oxide.

It is preferred that the photopolymerization initiator be used in combination with a reducing compound. Examples of the reducing compound may include: tertiary amines such as 2-(dimethylamino)ethyl methacrylate, ethyl 4-dimethylaminobenzoate, N-methyldiethanolamine, dimethylaminobenzaldehyde, and terephthalaldehyde; sulfur-containing compounds such as 2-mercaptobenzoxazole, 1-decanethiol, thiosalicylic acid, and thiobenzoic acid; and N-phenylalanine.

In addition, in order to further increase the activity of the photopolymerization initiator, a mode of adding a photoacid generator is also preferred. Examples of the photoacid generator include a diaryliodonium salt-based compound, a sulfonium salt-based compound, a sulfonic acid ester compound, a halomethyl-substituted S-triazine derivative, and a pyridinium salt-based compound. When the photoacid generator is used, the photopolymerization initiator is preferably an α-diketone such as camphorquinone, and is more preferably used in combination with a reducing compound such as 4-dimethylaminobenzoic acid.

On the other hand, examples of the thermal polymerization initiator may include: peroxides such as benzoyl peroxide, p-chlorobenzoyl peroxide, tert-butyl peroxy-2-ethylhexanoate, tert-butyl peroxydicarbonate, and diisopropyl peroxydicarbonate; and azo compounds such as azobisisobutyronitrile.

In addition, an example of the chemical polymerization initiator is a system in which the peroxide to be used in the thermal polymerization initiator, and the tertiary amine exemplified as the reducing compound in the photopolymerization initiator are used in combination.

In each of the polymerizable compositions, the blending amount of the polymerization initiator is preferably from 0.01 part by mass to 5 parts by mass, more preferably from 0.1 part by mass to 5 parts by mass, with respect to 100 parts by mass of the polymerizable monomer. The polymerization initiator is used in an amount that falls within this range and that allows a desired color tone of the polymerizable composition to be achieved.

Further, as the filler, one to be used as a filler for a composite resin in the field of dentistry may be used without any limitation. Specific examples thereof include inorganic powders of amorphous silica, silica-zirconia, silica-titania, quartz, alumina, barium glass, zirconia, titania, lanthanoids, colloidal silica, and the like. These inorganic powders may be subjected to surface treatment with a silane coupling agent or the like. Further, organic powders and organic-inorganic composite powders may also be used. In the dental filling and restorative material kit according to this embodiment, spherical complex oxide particles produced by a method disclosed in JP 58-110414 A, JP 58-156524 A, and the like are particularly suitably used as the filler.

In each of the polymerizable compositions, the blending amount of the filler is preferably from 200 parts by mass to 1,900 parts by mass, more preferably from 300 parts by mass to 900 parts by mass, with respect to 100 parts by mass of the polymerizable monomer. The filler is used in an amount that falls within this range and that allows a desired color tone of the polymerizable composition to be achieved.

The polymerizable compositions each containing the polymerizable monomer, the polymerization initiator, and the filler are each adjusted to a desired color tone by blending a colorant. The colorant to be used may be a pigment, or may be a dye. Examples of the pigment may include: white pigments such as titanium oxide, zinc oxide, and zirconium oxide as white pigments; red pigments such as red iron oxide, molybdenum red, and cromophtal red; yellow pigments such as yellow iron oxide, titanium yellow, chromium oxide, and cromophtal yellow; blue pigments such as cobalt blue, ultramarine, iron blue, cromophtal blue, and phthalocyanine blue; and black pigments such as black iron oxide and carbon black. On the other hand, examples of the dye may include: red dyes such as KAYASET RED G (Nippon Kayaku Co., Ltd.) and KAYASET RED B (Nippon Kayaku Co., Ltd.); yellow dyes such as KAYASET Yellow 2G and KAYASET Yellow GN; and dyes such as KAYASET Blue N, KAYASET Blue G, and KAYASET Blue B. In consideration of color tone stability in the mouth, it is preferred to use a water-insoluble pigment rather than a water-soluble dye.

In general, when the pigment is used as the colorant, the average particle size of the pigment is generally about 1 μm or less. As necessary, a commercially available pigment may be finely pulverized so as to have a small particle diameter. In addition, the pigment may be added in the form of a dispersion to a blend in order for the pigment to be easily mixed with other components of the dental filling and restorative material. For example, the pigment may be used as a master batch obtained by dispersing the pigment in a low-viscosity liquid such as a reactive diluent, or by dispersing the pigment in powder such as inorganic particles.

A plurality of those colorants may be used in combination to adjust each of the polymerizable compositions so as to have the following values for $a^*$, $b^*$, and $L^*$, which are determined to conform to those of the surroundings of the tooth to be restored: $a^*$ falls within the range of from −5.0 to 3.0, $b^*$ falls within the range of from −10 to 20, the $L^*$ of the polymerizable composition for a dentin restorative material is from 50 to 75, and the $L^*$ of the polymerizable composition for an enamel restorative material is from 40 to 55. In addition, the contrast ratio may also be adjusted with the colorant, and is preferably adjusted with a white pigment.

In general, when the pigment is used as the colorant, the total blending amount thereof is preferably from 0.0005 part by mass to 0.5 part by mass, more preferably from 0.001 part by mass to 0.3 part by mass, with respect to 100 parts by mass of the polymerizable monomer.

In addition, as necessary, any other known additive may be blended in each of the polymerizable compositions included in the dental filling and restorative material kit according to this embodiment. Specific examples thereof include a polymerization inhibitor, a UV absorber, water, an organic solvent, and a thickener. In terms of composition, the polymerizable compositions included in the dental filling and restorative material kit according to this embodiment are each a material similar to a composite resin to be used in a photopolymerization-type dental filling and restorative material kit in which i) a filling and restorative material (composite resin), and ii) a pretreatment agent (primer) or an adhesive (bonding material) are used in combination. In addition, the polymerizable compositions included in the dental filling and restorative material kit according to this embodiment are fundamentally different materials from the primer and the bonding material, which have a main function/role of improving adhesiveness between the composite resin and a tooth surface and contain large amounts of water and an organic solvent, in view of the main function/role of the materials and whether or not water and the organic solvent are contained. That is, in the polymerizable compositions included in the dental filling and restorative material kit according to this embodiment, the contents of water and the organic solvent may be generally 0 parts by mass (that is, no water and no organic solvent are contained) as in the above-mentioned composite resin. However, the polymerizable compositions included in the dental filling and restorative material kit according to this embodiment may contain, as necessary, small amounts of water and/or the organic solvent. The contents of water and/or the organic solvent in this case fall within, for example, preferably the range of from 0 parts by mass to 1 part by mass, more preferably the range of from 0 parts by mass to 0.5 part by mass, with respect to 100 parts by mass of the polymerizable monomer component.

Next, a method of using the dental filling and restorative material kit according to this embodiment is described.

The dental filling and restorative material kit according to this embodiment may be used for any tooth restoration, and is used in accordance with a general method of using a composite resin for filling. A specific example thereof is a method involving treating a cavity of a tooth to be restored with an appropriate pretreatment agent or adhesive, then directly filling the cavity with the polymerizable compositions included in the dental filling and restorative material kit according to this embodiment, forming the shape of a tooth, and then polymerizing and curing the polymerizable compositions through irradiation with intense light through the use of a specialized photoirradiation device.

The dental filling and restorative material kit according to this embodiment may be used in a mode in which the polymerizable composition for an enamel restorative material is layered on the polymerizable composition for a dentin restorative material, or on a dentin restorative material obtained by curing the polymerizable composition for a dentin restorative material. In addition, for the purpose of facilitating shape formation, the following may be performed without any problems: the polymerizable composition for an enamel restorative material is thinly filled on a lingual side, the polymerizable composition for a dentin restorative material is layered on the cured enamel restorative material, and the polymerizable composition for an enamel restorative material is further layered. In addition, when the dental filling and restorative material kit according to this embodiment is used in actual restoration, which widely ranges from an incisal portion to a tooth cervical portion, the polymerizable composition for an enamel restorative material may be not layered on part of the polymerizable composition for a dentin restorative material in order to conform the color tones of a human tooth to be restored and the restorative material to each other. For example, in the restoration of the incisal portion including a large amount of enamel, the polymerizable composition for an enamel restorative material may be thickly layered on the polymerizable composition for a dentin restorative material. On the other hand, in the restoration of the tooth cervical portion including thin enamel and thick dentin, part of the polymerizable composition for a dentin restorative material (or dentin restorative material) may be not covered with the polymerizable composition for an enamel restorative material (or enamel restorative material), and part of the polymerizable composition for a dentin restorative material (or dentin restorative material) may be present at the surface layer.

The polymerizable composition for a dentin restorative material and polymerizable composition for an enamel restorative material to be used in the dental filling and restorative material kit according to this embodiment are desirably prepared so as to well conform to the enamel and dentin of a human tooth in consideration of variations among sites and individuals to be subjected to the restoration as well. To this end, it is appropriate that: about 2 to 20 kinds of polymerizable compositions having different color tones be prepared for each of the polymerizable composition for a dentin restorative material and the polymerizable composition for an enamel restorative material; and at the time of use, at least one kind of polymerizable composition for a dentin restorative material and at least one kind of polymerizable composition for an enamel restorative material differing from each other in color tone and satisfying the relationship of a refractive index difference $(n_D{}^a - n_D{}^b)$ of 0.005 or more be selected from these polymerizable compositions and used. Kinds that are needed are appropriately adopted from Group A (reddish brown), Group B (reddish yellow), C Group (gray), and D Group (reddish gray) provided in a general shade guide ("VITAPAN Classical" is most commonly used). Specifically, in order to well conform to the hue of a human tooth, in the color tone of a 1-mm cured body of a polymerizable composition under a black background condition in color measurement in the CIELab color system, a* is set within the range of from −5.0 to 3.0, more suitably within the range of from −4.0 to 2.0. On the other hand, b* is set within the range of from −10 to 20, more suitably within the range of from −9 to 19.

Thicknesses at which the polymerizable composition for a dentin restorative material, and polymerizable composition for an enamel restorative material included in the dental filling and restorative material kit according to this embodiment are filled may be appropriately adjusted depending on a restoration site. In general restoration, the polymerizable composition for a dentin restorative material is filled at 3 mm or less, and the polymerizable composition for an enamel restorative material is filled at a thickness of 2 mm or less. The dental filling and restorative material kit according to this embodiment is particularly suited to restoration including an incisal portion like a class IV cavity in which the polymerizable composition for a dentin restorative material is thinly filled. That is, in the incisal portion, in general, the polymerizable composition for a dentin restorative material is filled at a thickness of 1 mm or less, more preferably 0.5 mm or less, whereas the polymerizable composition for an enamel restorative material is filled at a thickness of from about 1 mm to 2 mm. When the polymerizable composition for a dentin restorative material is thinly filled and the polymerizable composition for an enamel restorative material is thickly filled as compared to the polymerizable composition for a dentin restorative material as just described, in general, the restoration is darkened, and the characteristic structure of the dentin (mamelon) is difficult to see, resulting in a reduction in aesthetics. However, when the dental filling and restorative material kit according to this embodiment is used, the problem of the reduction in lightness due to the layering of the enamel restoration portion can be ameliorated, the characteristic shape of the dentin can be reproduced, and restoration with good color tone conformability to a natural tooth can be achieved.

EXAMPLES

The present invention is more specifically described below byway of Examples, but the present invention is not limited to Examples described below. It should be noted that compounds used in Examples and Comparative Examples are shown below.
(1) Polymerizable Monomer
M-1: D2.6E (80)/3G (20)
Refractive index of polymer: 1.556
M-2: bis-GMA (60)/3G (40)
Refractive index of polymer: 1.546
M-3: UDMA (45)/D2.6E (35)/3G (20)
Refractive index of polymer: 1.530
M-4: UDMA (60)/3G (40)
Refractive index of polymer: 1.509
M-5: D2.6E (100)
Refractive index of polymer: 1.567

The values in the parentheses represent parts by mass, and the refractive index of each polymer represents the refractive index of a polymer produced by mixing and polymerizing a plurality of polymerizable monomers (e.g., D2.6E and 3G in M-1).
(2) Photopolymerization Initiator
Camphorquinone (CQ)
Ethyl N,N-dimethyl-p-benzoate (DMBE)
(3) Polymerization Inhibitor
Hydroquinone monomethyl ether (HQME)
(4) Filler
F-1: Filler obtained by mixing 60 parts by mass of a spherical silica zirconia filler (average particle diameter; 0.4 µm) and 40 parts by mass of silica titania fine particles (average particle diameter; 0.07 µm), followed by disintegration, and subjecting the resultant to surface treatment with γ-methacryloyloxypropyltrimethoxysilane. Refractive index: 1.52
F-2: Filler obtained by subjecting amorphous silica zirconia (average particle diameter; 1.2 µm) to surface treatment with γ-methacryloyloxypropyltrimethoxysilane. Refractive index: 1.53
F-3: Filler obtained by subjecting spherical silica zirconia (average particle diameter; 0.2 µm) to surface treatment with γ-methacryloyloxypropyltrimethoxysilane. Refractive index: 1.52
F-4: Organic-inorganic composite filler, which is obtained by mixing 40 parts by mass of bis-GMA, 60 parts by mass of 3G, 1 part by mass of azobisisobutyronitrile, and 300 parts by mass of F-3, followed by defoaming, subjecting the resultant to thermal polymerization, and then subjecting the resultant to milling and surface treatment. Average particle diameter: 30 µm. Refractive index: 1.52
(5) Colorant
White pigment (titanium dioxide)
Yellow pigment (Pigment Yellow)
Red pigment (Pigment Red)
Blue pigment (Pigment Blue)

In addition, various physical properties measured in Examples and Comparative Examples described below were measured by the following methods.
(1) Measurement of Contrast Ratio
A polymerizable composition was filled into a polyacetal mold having a thickness of 1 mm and having formed therein a through-hole having a diameter 7 mm, and a polypropylene film was brought into pressure contact therewith. The resultant was subjected to photoirradiation with a dental photoirradiation device (TOKUSO POWER LITE, manufactured by Tokuyama Dental Corporation; optical output density: 700 mW/cm$^2$) for 30 seconds. The resultant cured body was irradiated with standard light C and the color tone of reflected light in this case was measured using a colorimeter (manufactured by Tokyo Denshoku Co., Ltd.: TC-1800MKII) under each of white background and black background conditions. A contrast ratio was calculated from the resultant respective Y values using the following equation.
C (contrast ratio)=Yb (Y value against black background)/Yw (Y value against white background)
(2) Measurement of Color Tone
Measurement was performed as specified in JIS Z8729. Specifically, a polymerizable composition was filled into a polyacetal mold having a thickness of 1.0 mm and having formed therein a through-hole having a diameter of 7 mm, and a polypropylene film was brought into pressure contact therewith. The resultant was subjected to photoirradiation with a dental photoirradiation device (TOKUSO POWER LITE, manufactured by Tokuyama Dental Corporation; optical output density: 700 mW/cm$^2$) for 30 seconds. The resultant cured body was irradiated with standard light C and the color tone of reflected light in this case was measured using a colorimeter (manufactured by Tokyo Denshoku Co., Ltd.: TC-1800MKII) under a black background condition. A lightness L*, and chromaticity a* and b* expressed in the CIELab color system were each obtained.
(3) Measurement of Color Tone in Layered Configuration
Measurement was performed as specified in JIS Z8729. Specifically, a polymerizable composition (A) for a dentin restorative material was filled into a polyacetal mold having a thickness of 0.5 mm and having formed therein a through-hole having a diameter of 7 mm, and a polypropylene film was brought into pressure contact therewith. The resultant was subjected to photoirradiation with a dental photoirradiation device (TOKUSO POWER LITE, manufactured by Tokuyama Dental Corporation; optical output density: 700 mW/cm$^2$) for 30 seconds. The polypropylene film was peeled off, another polyacetal mold having a thickness of 0.5 mm and having formed therein a through-hole having a diameter of 7 mm was placed on the resultant, a polymerizable composition (B) for an enamel restorative material was filled thereinto, and a polypropylene film was brought into pressure contact therewith. The resultant was subjected to photoirradiation with the dental photoirradiation device for 30 seconds. The surface of the polymerizable composition (B) for an enamel restorative material of the resultant cured body was irradiated with standard light C and the color tone of reflected light in this case was measured using a colorimeter (manufactured by Tokyo Denshoku Co., Ltd.: TC-1800MKII) under a black background condition. A lightness L*, and chromaticity a* and b* expressed in the CIELab color system were each obtained.
(4) Color Tone Change by Layering
A change in color tone of a cured body (dentin restorative material) of a polymerizable composition for a dentin restorative material by the layering and curing of a polymerizable composition for an enamel restorative material was calculated by the following equation.

$$\Delta L^* = L^*_S - L^*_I$$

In the equation, $L^*_S$ represents the L* of a cured body (thickness: 1 mm) of the polymerizable composition for a dentin restorative material, and $L^*_I$ represents the L* of a cured body obtained by layering, on a cured body (thickness: 0.5 mm) of the polymerizable composition for a dentin restorative material, the polymerizable composition for an enamel restorative material at a thickness of 0.5 mm. A negative larger value for ΔL* shows that the lightness is reduced by the layering, and shows that the layering of the polymerizable composition for an enamel restorative material shields the color tone of the cured body (dentin restorative material) of the polymerizable composition for a dentin restorative material.

(5) Evaluation of Aesthetics

Aesthetics was evaluated for each of a class I cavity having a lining, which was hardly influenced by a background color, and a class IV cavity having no lining, which was liable to be influenced by a background color. Specifically, as the class I cavity, a box-shaped cavity (about 4 mm horizontal, about 3 mm vertical, and about 2 mm deep) was formed at the center of an occlusal surface through the use of the first molar of M32 A3 of Endura Posterio (trade name, manufactured by Shofu Inc.), and was filled with an adjusted polymerizable composition for a dentin restorative material, which was shaped and then cured. A polymerizable composition for an enamel restorative material was filled and cured thereon, followed by polishing.

In addition, as the class IV cavity, a box-shaped cavity (about 3 mm horizontal and about 4 mm vertical) was formed in a mesial direction through the use of A3 of VITAPAN classical (trade name, manufactured by VITA Zahnfabrik), and was filled with a prepared polymerizable composition for a dentin restorative material, which was shaped into the shape of a mamelon and then cured. A polymerizable composition for an enamel restorative material was filled and cured thereon, followed by polishing. Aesthetics at each restoration site was evaluated as follows: in the class I cavity, color tone conformability to the tooth to be restored was evaluated, and in the class IV cavity, color tone conformability to the tooth to be restored and the visibility of the mamelon were evaluated, in accordance with the following respective criteria.

<Color Tone Conformability to Tooth to be Restored>
A: The color tone of the restorative material well conforms to that of the surroundings.
B: The color tone of the restorative material conforms to that of the surroundings, but the restoration site is recognizable.
C: The color tone of the restorative material is distinctly darker than and does not conform to that of the surroundings.

<Visibility of Mamelon>
A: The shape of the mamelon can be visually recognized. In addition, a restoration closer to a natural tooth is obtained as compared to the following evaluation B.
B: The shape of the mamelon can be visually recognized.
C: The shape of the mamelon cannot be visually recognized.

Example 1

In a dark place, 100 parts by mass of the polymerizable monomer M-1 having dissolved therein 0.2 part by mass of CQ, 0.5 part by mass of DMBE, and 0.15 part by mass of HQME, and 400 parts by mass of the filler F-1 were mixed and kneaded to prepare a polymerizable composition. An appropriate amount of a pigment was added to the polymerizable composition so as to have a contrast ratio C and color tone $L^*$, $a^*$, and $b^*$ shown in Table 1, and the contents were sufficiently mixed and kneaded, followed by defoaming. The resultant was defined as a polymerizable composition P1. In addition, a polymerizable composition prepared in the same manner as the polymerizable composition P1 except that the kinds and blending amounts of the polymerizable monomer and filler used were changed to conditions shown in Table 1 was defined as a polymerizable composition P2. Each of the polymerizable compositions was in a paste form. Various evaluations were performed by the methods described above using the polymerizable composition P1 as the polymerizable composition (A) for a dentin restorative material, and the polymerizable composition P2 as the polymerizable composition (B) for an enamel restorative material. The results are shown in Table 2.

Examples 2 to 9 and 11 to 15, and Comparative Examples 1 to 3

Polymerizable compositions P3 to P17 were prepared in the same manner as the polymerizable composition P1 except that the kinds and blending amounts of the polymerizable monomer and filler used were changed to conditions shown in Table 1. Each of the polymerizable compositions was in a paste form. Next, various evaluations were performed using combinations as shown in Table 2 of a polymerizable composition used as the polymerizable composition (A) for a dentin restorative material and a polymerizable composition used as the polymerizable composition (B) for an enamel restorative material. The results of the evaluations are shown in Table 2.

Example 10 and Comparative Example 4

Polymerizable compositions P1', P2, P4, and P10' were prepared in the same manner as the polymerizable composition P1 except that the kinds and blending amounts of the polymerizable monomer and filler used were changed to conditions shown in Table 1. Each of the polymerizable compositions was in a paste form. Next, various evaluations were performed using combinations of those polymerizable compositions as shown in Table 2. It should be noted that the evaluation of "color tone in layered configuration" shown in Table 2 was performed in accordance with the measurement procedure of the section "(3) Measurement of Color Tone in Layered Configuration" described above except that the thickness of the polymerizable composition for a dentin restorative material was changed to 0.5 mm and the thickness of the polymerizable composition for an enamel restorative material was changed to 1.0 mm. The results are shown in Table 2. In addition, $\Delta L^*$ was calculated in accordance with the evaluation procedure of the section "(4) Color Tone Change by Layering" described above except that the thickness of the cured body of the polymerizable composition for a dentin restorative material used in the determination of the $L^*_S$ value (that is, the polymerizable composition P1' used in Example 10 and the polymerizable composition P10' used in Comparative Example 4) was changed to 1.5 mm. The results are shown in Table 2.

TABLE 1

| Polymerizable composition | Polymerizable monomer (parts by mass) | Filler (parts by mass) | C | $L^*$ | $a^*$ | $b^*$ |
|---|---|---|---|---|---|---|
| P1 | M-1 (100) | F-1 (400) | 0.60 | 57.2 | −1.6 | 6.0 |
| P2 | M-2 (100) | F-1 (400) | 0.45 | 49.6 | −1.0 | 1.0 |
| P3 | M-3 (100) | F-1 (400) | 0.46 | 47.2 | −0.9 | 1.0 |
| P4 | M-4 (100) | F-1 (400) | 0.45 | 47.8 | −1.0 | 0.9 |
| P5 | M-1 (100) | F-1 (400) | 0.72 | 72.4 | −1.5 | 6.1 |
| P6 | M-3 (100) | F-1 (400) | 0.31 | 42.5 | −0.7 | 1.5 |
| P7 | M-1 (100) | F-1 (280)/F-2 (120) | 0.60 | 57.8 | −1.5 | 6.2 |
| P8 | M-1 (100) | F-4 (240)/F-3 (160) | 0.61 | 56.9 | −1.5 | 6.1 |
| P9 | M-2 (100) | F-4 (200)/F-3 (200) | 0.44 | 46.2 | −0.9 | 1.1 |
| P10 | M-4 (100) | F-1 (400) | 0.60 | 57.3 | −1.6 | 5.9 |

TABLE 1-continued

| Polymerizable composition | Polymerizable monomer (parts by mass) | Filler (parts by mass) | C | L* | a* | b* |
|---|---|---|---|---|---|---|
| P11 | M-1 (100) | F-1 (400) | 0.45 | 45.8 | −0.9 | 1.1 |
| P12 | M-5 (100) | F-1 (400) | 0.60 | 58.2 | −1.4 | 6.3 |
| P13 | M-1 (100) | F-1 (400) | 0.77 | 75.3 | −1.5 | 6.2 |
| P14 | M-1 (100) | F-1 (400) | 0.53 | 51.1 | −1.5 | 6.0 |
| P15 | M-3 (100) | F-1 (400) | 0.55 | 53.7 | −0.8 | 1.2 |
| P16 | M-3 (100) | F-1 (400) | 0.28 | 41.2 | −1 | 1.1 |
| P17 | M-1 (100) | F-1 (400) | 0.28 | 40.5 | −1.1 | 1.3 |
| P1' | M-1 (100) | F-1 (400) | 0.75 | 57.5 | −1.0 | 6.9 |
| P10' | M-4 (100) | F-1 (400) | 0.76 | 57.8 | −0.9 | 7.0 | polymer of the polymerizable monomer contained in the polymerizable composition (B) for an enamel restorative material was less than 0.005, the lightness of the dentin portion restorative material was reduced by the layering of the enamel portion restorative material, and a dark restoration was obtained as a result of the influence of the background color in the restoration of the class IV cavity. Accordingly, the visibility of the mamelon was low.

As understood from the results of Example 10 shown in Table 2, when the refractive index difference $(n_D^a-n_D^b)$ is 0.005 or more, even if the enamel restorative material is thickly filled on the dentin restorative material, the reduction in lightness is small, and the visibility of the mamelon in the incisal portion is high.

TABLE 2

| | Polymerizable composition (A) for dentin restorative material | | Polymerizable composition (B) for enamel restorative material | | Difference between refractive indices of polymers | Color tone in layered configuration | | | | Evaluation of aesthetics | | |
|---|---|---|---|---|---|---|---|---|---|---|---|---|
| | | | | | | | | | | Class I cavity | Class IV cavity | |
| | Kind | C | Kind | C | polymers | L* | a* | b* | ΔL* | Color tone conformability | Visibility of mamelon | Color tone conformability |
| Example 1 | P1 | 0.60 | P2 | 0.45 | 0.010 | 54.2 | −1.4 | 3.4 | −3.0 | A | A | A |
| Example 2 | P1 | 0.60 | P3 | 0.46 | 0.026 | 54.9 | −1.4 | 3.4 | −2.3 | A | A | A |
| Example 3 | P1 | 0.60 | P4 | 0.45 | 0.047 | 55.3 | −1.3 | 3.6 | −1.9 | A | A | A |
| Example 4 | P5 | 0.72 | P3 | 0.46 | 0.026 | 69.1 | −1.3 | 3.5 | −3.3 | A | B | A |
| Example 5 | P1 | 0.60 | P6 | 0.31 | 0.026 | 53.4 | −1.3 | 3.8 | −3.8 | A | B | A |
| Example 6 | P5 | 0.72 | P6 | 0.31 | 0.026 | 67.8 | −1.2 | 3.9 | −4.6 | A | B | A |
| Example 7 | P7 | 0.60 | P3 | 0.46 | 0.026 | 55.0 | −1.3 | 3.7 | −2.8 | A | A | A |
| Example 8 | P8 | 0.61 | P2 | 0.45 | 0.010 | 54.8 | −1.3 | 3.7 | −2.1 | A | A | A |
| Example 9 | P1 | 0.60 | P9 | 0.44 | 0.010 | 54.4 | −1.3 | 3.5 | −2.8 | A | A | A |
| Example 10 | P1' | 0.75 | P2 | 0.45 | 0.010 | 52.4 | −1.0 | 2.9 | −5.1 | A | B | A |
| Example 11 | P12 | 0.60 | P4 | 0.45 | 0.058 | 56.1 | −1.2 | 3.6 | −2.1 | A | A | A |
| Example 12 | P13 | 0.77 | P3 | 0.46 | 0.026 | 70.8 | −1.3 | 3.5 | −4.5 | A | B | B |
| Example 13 | P14 | 0.53 | P3 | 0.46 | 0.026 | 48.1 | −1.3 | 3.4 | −3.0 | A | B | B |
| Example 14 | P1 | 0.60 | P15 | 0.55 | 0.026 | 55.4 | −1.3 | 3.6 | −1.8 | A | B | B |
| Example 15 | P1 | 0.60 | P16 | 0.28 | 0.026 | 51.9 | −1.4 | 3.6 | −5.3 | A | B | B |
| Comparative Example 1 | P10 | 0.60 | P4 | 0.45 | 0 | 50.9 | −1.4 | 3.4 | −6.4 | A | C | A |
| Comparative Example 2 | P10 | 0.60 | P3 | 0.46 | −0.021 | 51.1 | −1.3 | 3.3 | −6.2 | A | C | A |
| Comparative Example 3 | P10 | 0.60 | P11 | 0.45 | −0.047 | 50.2 | −1.3 | 3.3 | −7.1 | A | C | A |
| Comparative Example 4 | P10' | 0.76 | P4 | 0.45 | 0 | 48.8 | −0.9 | 2.8 | −9.0 | A | C | A |

As understood from the results of Examples 1 to 9 and 11 to 15 shown in Table 2, when the refractive index $n_D^b$ of the polymer of the polymerizable monomer contained in the polymerizable composition (B) for an enamel restorative material was lower than the refractive index $n_D^a$ of the polymer of the polymerizable monomer contained in the polymerizable composition (A) for a dentin restorative material, and their refractive index difference $(n_D^a-n_D^b)$ was 0.005 or more, the reduction in lightness of the dentin restorative material was small even if the enamel restorative material was layered, and restoration with high aesthetics was able to be performed without being influenced by the background color even in the restoration of the class IV cavity having no lining.

On the other hand, as understood from the results of Comparative Examples 1 to 3 shown in Table 2, when the refractive index difference $(n_D^a-n_D^b)$ between the refractive index $n_D^a$ of the polymer of the polymerizable monomer contained in the polymerizable composition (A) for a dentin restorative material and the refractive index $n_D^b$ of the On the other hand, as understood from the results of Comparative Example 4 shown in Table 2, when the refractive index difference $(n_D^a-n_D^b)$ is less than 0.005, even if the enamel restorative material is thickly filled on the dentin restorative material, the reduction in lightness is larger, and the visibility of the mamelon in the incisal portion is lower.

The invention claimed is:

1. A dental filling and restorative material kit, comprising:
    a polymerizable composition (A) for a dentin restorative material for restoring a dentin portion; and
    a polymerizable composition (B) for an enamel restorative material to be layered on the dentin restorative material,
    wherein the polymerizable composition (A) for a dentin restorative material and the polymerizable composition (B) for an enamel restorative material have different color tones,
    wherein the polymerizable composition (A) comprises a polymerizable monomer (a) and 200 to 1900 parts by mass of a filler, with respect to 100 parts by mass of the polymerizable monomer (a), and the polymerizable composition (B) comprises a polymerizable monomer (b) and 200 to 1900 parts by mass of a filler, with respect to 100 parts by mass of the polymerizable monomer (b), wherein a difference ($n_D^a - n_D^b$) between a refractive index $n_D^a$ of a polymer of the polymerizable monomer (a) in the polymerizable composition (A) for the dentin restorative material and a refractive index $n_D^b$ of a polymer of the polymerizable monomer (b) in the polymerizable composition (B) for the enamel restorative material is 0.005 or more, wherein contents of at least one element selected from the group consisting of water and an organic solvent is within the range of from 0 parts by mass to 1 part by mass with respect to 100 parts by mass of the polymerizable composition (A) for the dentin restorative material, and wherein contents of at least one element selected from the group consisting of water and an organic solvent is within the range of from 0 parts by mass to 1 part by mass with respect to 100 parts by mass of the polymerizable composition (B) for the enamel restorative material.

2. The dental filling and restorative material kit according to claim 1, wherein the dental filling and restorative material kit consists of the polymerizable composition (A) for the dentin restorative material and the polymerizable composition (B) for the enamel restorative material.

3. The dental filling and restorative material kit according to claim 1,
wherein a 1-mm cured body of the polymerizable composition (A) for the dentin restorative material has a contrast ratio of from 0.55 to 0.75, and
wherein a 1-mm cured body of the polymerizable composition (B) for the enamel restorative material has a contrast ratio of from 0.30 to 0.54.

4. The dental filling and restorative material kit according to claim 1,
wherein contents of both water as well as the organic solvent are within the range of 0 parts by mass to 1 part by mass with respect to 100 parts by mass of the polymerizable composition (A) for the dentin restorative material, and
wherein contents of both water as well as the organic solvent are within the range of 0 parts by mass to 1 part by mass with respect to 100 parts by mass of the polymerizable composition (B) for the enamel restorative material.

5. The dental filling and restorative material kit according to claim 1,
wherein the polymerizable composition (A) does not comprise water, and
wherein the polymerizable composition (B) does not comprise the organic solvent.

6. A dental filling and restorative material kit according to claim 1,
wherein the polymerizable composition (A) for the dentin restorative material comprises no water and no organic solvent, and
wherein the polymerizable composition (B) for the enamel restorative material comprises no water and no organic solvent.

7. The dental filling and restorative material kit according to claim 1,
wherein the polymerizable composition (A) does not comprise water, and
wherein the polymerizable composition (B) does not comprise water.

8. The dental filling and restorative material kit according to claim 1,
wherein the polymerizable composition (A) does not comprise the organic solvent, and
wherein the polymerizable composition (B) does not comprise the organic solvent.

9. The dental filling and restorative material kit according to claim 1,
wherein the polymerizable composition (A) does not comprise the organic solvent, and
wherein the polymerizable composition (B) does not comprise water.

* * * * *